United States Patent [19]
Kondo et al.

[11] 4,456,380
[45] Jun. 26, 1984

[54] TEST SYSTEM FOR IDENTIFYING BACTERIA

[75] Inventors: Takashi Kondo, Nagaokakyo; Kiyotaka Takagi, Kyoto; Taichiro Nishiyama, Osaka, all of Japan

[73] Assignee: Fujisawa Pharmaceutical Co., Ltd., Japan

[21] Appl. No.: 288,146

[22] Filed: Jul. 29, 1981

[30] Foreign Application Priority Data

Aug. 1, 1980 [JP] Japan .................. 55-106587

[51] Int. Cl.³ .................................. G01J 3/50
[52] U.S. Cl. ........................... 356/418; 364/526
[58] Field of Search ............. 356/51, 409, 410, 411, 356/414, 416, 418, 419, 432, 436; 435/291; 422/68; 364/499, 526

[56] References Cited

U.S. PATENT DOCUMENTS 3,627,431 12/1971 Komarniski .................. 356/409
4,083,367 4/1978 Portner et al. ................ 356/51 X

FOREIGN PATENT DOCUMENTS 2451769 5/1975 Fed. Rep. of Germany ...... 356/432
55-125436 9/1980 Japan .......................... 356/414
2014305 8/1979 United Kingdom ............. 356/409

Primary Examiner—F. L. Evans
Attorney, Agent, or Firm—Jordan B. Bierman; Linda Bierman

[57] ABSTRACT

A test system for identifying bacteria comprising a plate accommodating portion for placing therein a transparent culture plate having a plurality of cells, a light source assembly for applying a light to a specimen in each of the cells of the culture plate placed in the accommodating portion, a photoelectric element for converting to an electric signal the light reflected from or passing through the specimen, a rotary member having a plurality of filters for obtaining monochromatic lights of different wavelengths and a filter synchronizing signal generator and disposed between the light source assembly and the specimen, the rotary member being continuously rotatable at a predetermined speed in a predetermined direction to permit the filters to be selected one after another, and an operation control unit for deriving from the photoelectric element electric signals in response to the monochromatic lights passing through a specified number of the filters to determine the color of the specimen based on the signals.

11 Claims, 7 Drawing Figures

TEST SYSTEM FOR IDENTIFYING BACTERIA

BACKGROUND OF THE INVENTION

The present invention relates to a test system for identifying bacteria.

A test system for identifying bacteria is known by which a pure culture of bacteria collected from a test sample is further cultured for a specified period of time in a plurality of cells containing paper disks impregnated with various reagents, thereafter checking the disks for color reaction and determining the kind of the bacteria based on the combination of occurrence or absence of color reaction on the disks. With such a system, the colors are usually identified with the unaided eye, so that the test requires much time, and the test result may vary from person to person when determined by different persons.

SUMMARY OF THE INVENTION

An object of this invention is to provide a test system for identifying bacteria which is adapted to automatically determine the colors of specimens, such system preferably using paper disks impregnated with various reagents.

Another object of the invention is to provide a test system for identifying bacteria which is capable of determining the colors of such specimens accurately and efficiently.

These objects of the present invention can be fulfilled by a test system for identifying bacteria which includes a plate accommodating portion for placing therein a transparent culture plate having a plurality of cells, a light source assembly for applying light to a specimen in each of the cells of the culture plate placed in the accommodating portion, a photoelectric element for converting to an electric signal the light reflected from or passing through the specimen, a rotary member having a plurality of filters for obtaining monochromatic lights of different wavelengths and a filter synchronizing signal generator and disposed between the light source assembly and the specimen or between the specimen and the photoelectric element, the rotary member being continuously rotatable at a predetermined speed in a predetermined direction to permit the filters to be selected one after another, and an operation control unit for deriving from the photoelectric element electric signals in response to the monochromatic lights passing through a specified number of the filters to determine the color of the specimen based on the signals.

DESCRIPTION OF THE PREFERRED EMBODIMENT

The pesent test system identifies bacteria based on the same theory as conventionally adopted for identifying bacteria with use of disks and is adapted to automatically determine the colors of disks and, when desired, the kinds of bacteria. The conventional method of identifying bacteria will be described first.

For the identification of bacteria, a culture plate is used which includes a plurality of cells. Paper disks of different kinds impregnated with reagents are placed in the cells, one disk in each cell. The relation between the cells and the kinds of the disks is predetermined for the group of bacteria to be tested. A pure culture of bacteria collected from a test sample is placed into the cells along with the culture medium and further incubated for a period of time (18 to 24 hours). The disk in each of the cells is then checked for color reaction based on which of the two colors specified for the disk is formed on the disk, such that one of the two colors is interpreted as indicating a reaction taking place (positive) and the other color as indicative of no reaction (negative). In the case of some types of disks, a color forming reagent may be applied dropwise to the disk for the determination of color. Subsequently the occurrence and absence of color reactions for the cells are encoded according to a predetermined rule as will be described later, and the kind of the bacteria is determined from the resulting code with reference to a code table prepared in advance.

An embodiment of the invention will now be described with reference to the accompanying drawings.

Figure 1:
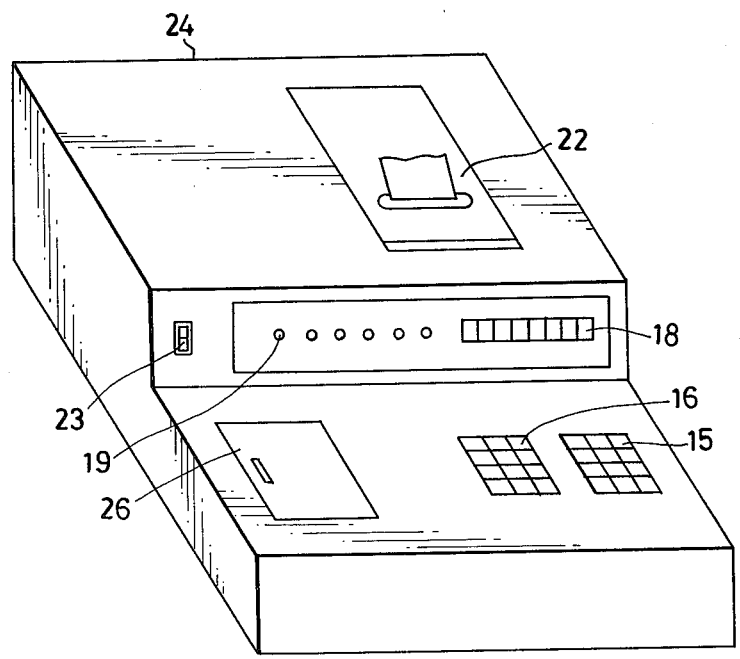
FIG. 1 is a perspective view showing a physical embodiment of the invention in its entirety.
Figure 2:
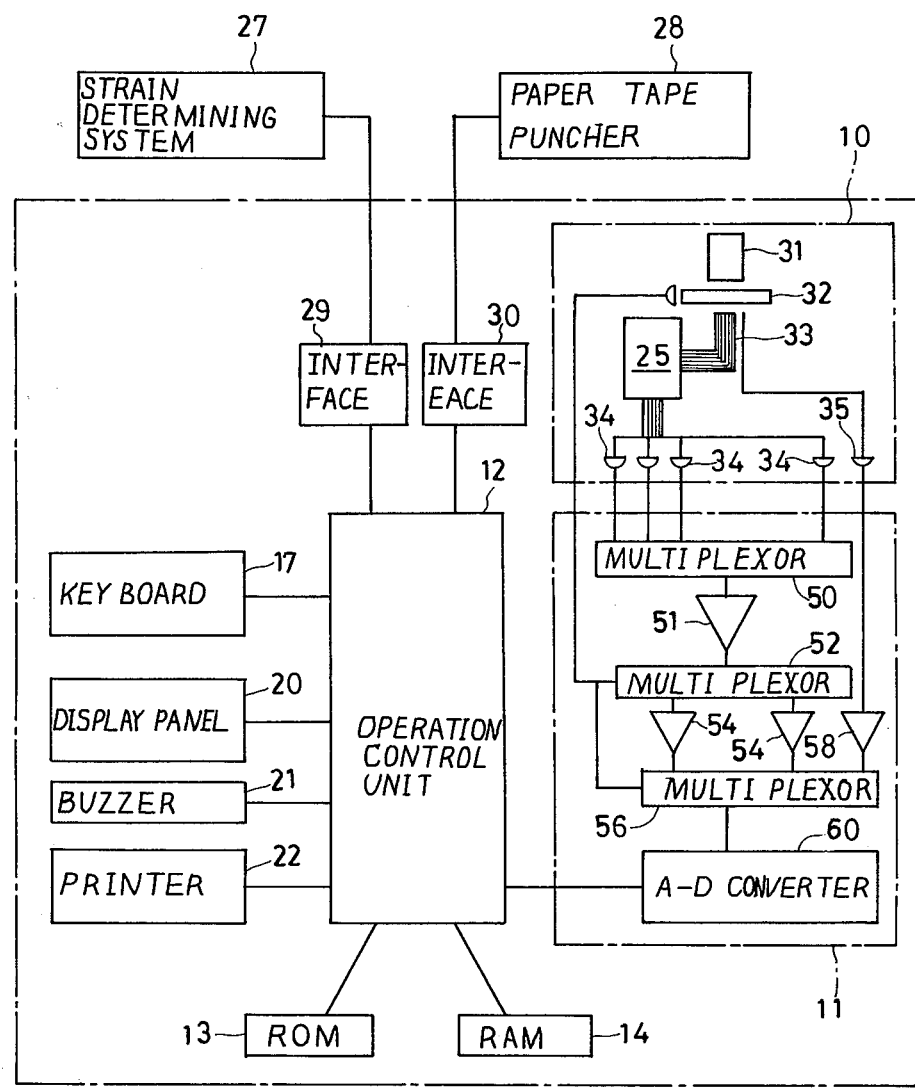
FIG. 2 is a block circuit diagram showing the overall interconnection of the elements of the system according to the present invention.

The test apparatus shown in FIG. 1 is used for identifying bacteria, such, for example, as the family Enterobacteriaceae and bacteria which do not utilize glucose. FIG. 2 shows the elements forming the system of such apparatus. The test system comprises a light measuring unit 10, an analog signal processing unit 11, an operation control unit 12 including a microcomputer, a read-only memory (ROM) 13 for storing a control program, a random access memory (RAM) 14 for storing data, a keyboard 17 having a ten-key arrangement 15 and function keys 16, a display panel 20 having an indicator 18 for displaying numbers of seven figures and various indicator lamps 19, a buzzer 21, a printer 22 and a power supply switch 23. These components are incorporated into a case 24, which has in its interior a plate accommodating portion (now shown) for placing a culture plate 25 therein. The plate 25 is placed into or out of the portion through an opening having a lid 26. When desired, the test system is connected to a strain determining system 27 or a paper tape puncher 28 through an interface 29 or 30 respectively.

Figure 3:
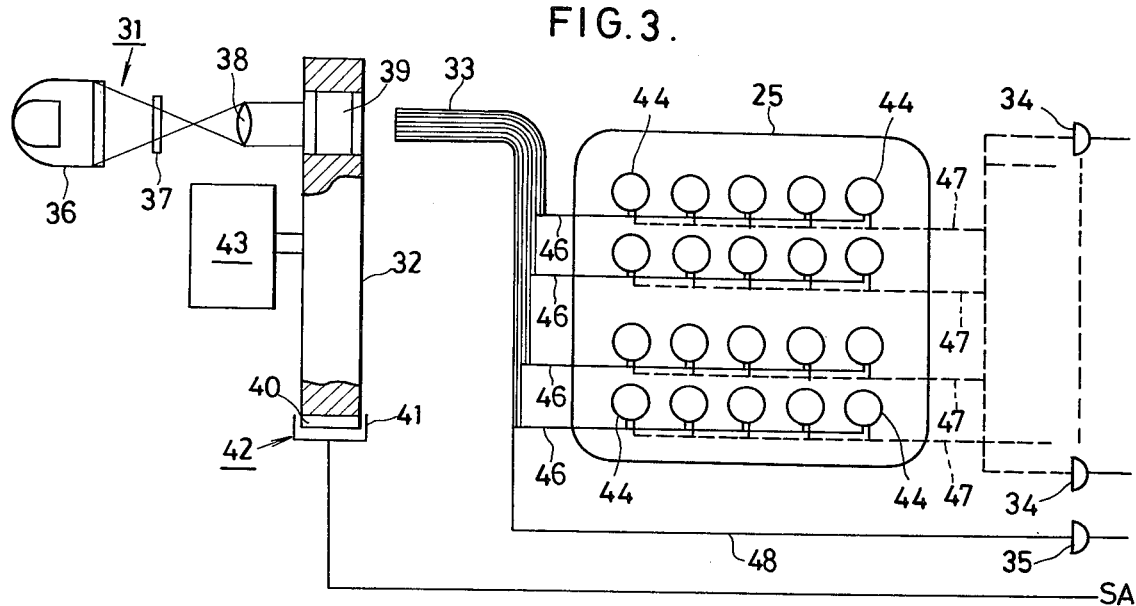
FIG. 3 is a diagram showing a light measuring unit and its relationship with other system elements.
Figure 4:
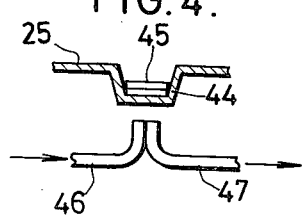
FIG. 4 is a sectional view showing a cell portion of a culture plate.

The light measuring unit 10 comprises a light source assembly 31, a rotary member (disk) 32, a group of optical fibers 33, a plurality of photoelectric elements 34, 35 and the culture plate 25. FIGS. 3 and 4 show details of the unit 10.

The light source assembly 31 comprises a halogen lamp 36 for giving off colorless light, a cold filter 37 for passing visible rays therethrough and absorbing thermal rays and a lens 38 and is adapted to apply parallel colorless rays to the rotary disk 32.

The rotary disk 32 is interposed between the light source assembly 31 and the group of optical fibers 33 and has six kinds of interference filters 39 in six equally divided outer peripheral portions of the disk for deriving monochromatic lights of different wavelengths. These filters are assigned No. 1 to No. 6 individually. The rotary disk 32 has a cutout 40 in its outer periphery. A photoelectric switch 41 is fixedly positioned for the cutout 40 independently of the rotary disk 32. The cutout and the switch constitute a filter synchronizing signal generator 42. The disk 32 is continuously rotated by a motor 43 at a predetermined speed in a predetermined direction. When the switch 41 emits a filter signal SA upon detecting the cutout 40, No. 1 to No. 6 filters 39 are selected in succession to apply monochromatic lights of different wavelengths to the group of optical fibers 33 during one turn of the disk 32 following the emission of the signal.

The culture plate 25 is made of transparent synthetic resin, glass or like material and has 20 cells 44 which are assigned No. 1 to No. 20 individually. As already described, paper disks (specimens) 45 impregnated with reagents are placed in the cells 44, one disk in each cell. Fifteen cells 44 with Nos. 1 to 15 are used for identifying the family Enterobacteriaceae, and eighteen cells 44 with Nos. 1 to 18 for bacteria which do not utilize glucose.

The fiber group 33 comprises twenty incident light optical fibers 46 for causing the monochromatic light passing through each of the filters 39 to fall on the disks 45 at the bottom of the cells 44, twenty reflected light optical fibers 47 for guiding the light reflected from the disks 45 to the corresponding twenty measuring photoelectric elements 34, and a single checking optical fiber 48 for guiding the monochromatic light through the filter 39 directly to the checking photoelectric element 35. Phototransistors and the like are useful as the elements 34, 35.

Figure 5:
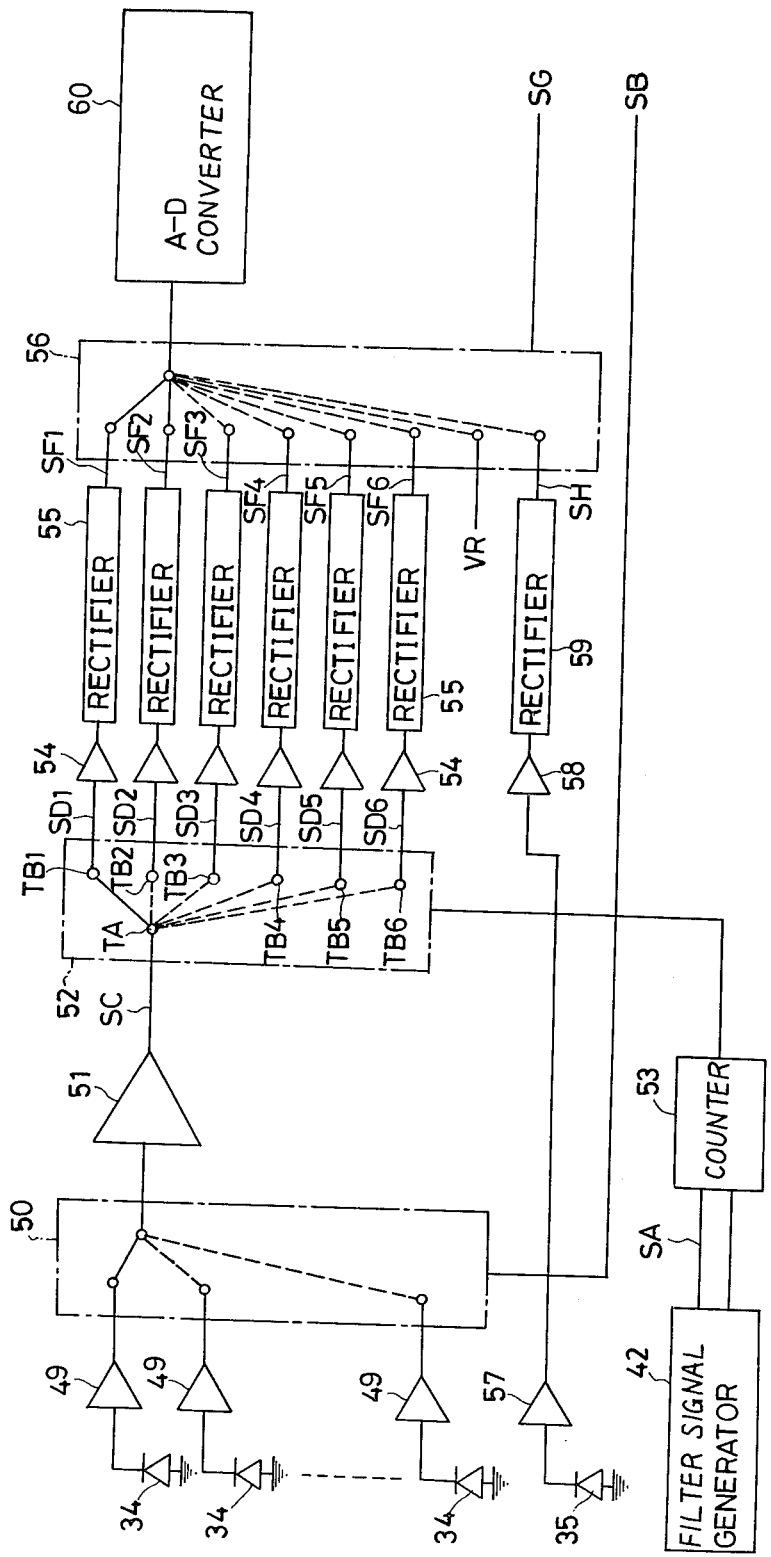
FIG. 5 is a diagram circuit showing the arrangement of the analog signal processing unit.
Figure 6:
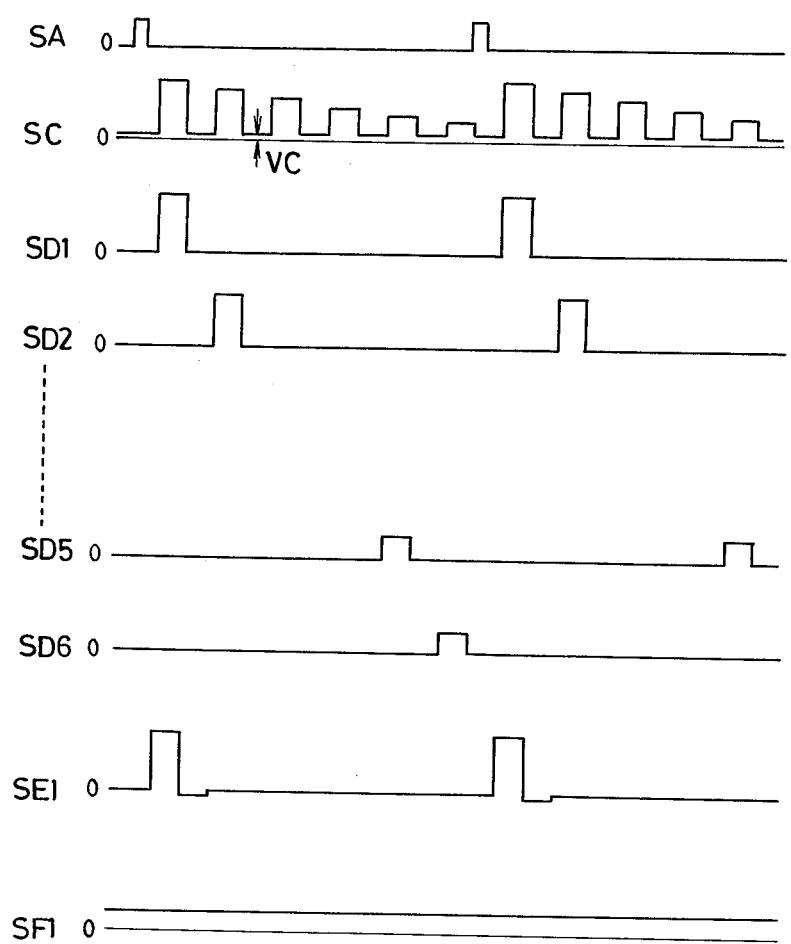
FIG. 6 is a time chart showing the relationship between signals handled by the components of the analog signal processing unit.

FIG. 5 shows the analog signal processing unit 11 in detail. The outputs of the twenty measuring photoelectric elements 34 of the measuring unit 10 are fed via amplifiers 49 to a cell selecting multiplexor 50. In response to a cell selecting signal SB from the control unit 12, the multiplexor 50 selects one of the outputs from the elements 34 and delivers the output to a signal distributing multiplexor 52 by way of an amplifier 51. Thus a signal SC proportional to the output of the selected element 34 is applied to the input terminal TA of the multiplexor 52. During the period following emission of a filter signal SA until the emission of another filter signal SA (i.e. during one turn of the rotary disk 32), for example, while No. 1 cell 44 is selected, the signal SC varies as shown in FIG. 6. Thus, while No. 1 filter 39 is selected, the signal SC is in proportion to the intensity of light reflected from the disk 45 in No. 1 cell 44 on which the monochromatic light through No. 1 filter 39 is incident. Similarly while Nos. 2 to 6 filters 39 are selected individually, the signal is in proportion to the intensities of the reflected lights resulting from the monochromatic lights through these filters. Indicated at VC in the signal SC in FIG. 6 is a component thereof due to a dark current of the photoelectric element 34. The signal distributing multiplexor 52 has six output terminals TB1 to TB6 corresponding to the filters 39 on the rotary disk 32. These output terminals TB1 to TB6 are selected one after another in timed relation to the output of a counter 53 which starts counting by being reset by the filter signal SA. Thus while No. 1 filter 39 is selected, the terminal TB1 is selected, and while Nos. 2 to 6 filters 39 are selected individually, one of the terminals TB2 to TB6 is selected in corresponding relation to the filters. Consequently these terminals TB1 to TB6 give output signals SD1 to SD6 as shown in FIG. 6. In other words, an output signal in proportion to the reflected light is available at one of the output terminals TB1 to TB6 only while the corresponding filter 39 is selected. In this way, the signals SD1 to SD6 in proportion to the reflected lights relating to the filters 39 are derived individually. The dark current component is eliminated from these signals SD1 to SD6, affording signals SE1 to SE6, which are fed through amplifiers 54 to rectifiers 55. The amplifier 54 corrects the difference in output level attributable to the wavelength characteristics of the light source assembly 31. Signals SF1 to SF6 resulting from the rectification are in proportion to the reflected lights relating to the corresponding filters 39 and are fed to a filter selecting multiplexor 56, which further receives a reference voltage VR for detecting deterioration of the lamp 36 and also the output of the checking photoelectric element 35 via amplifiers 57, 58 and a rectifier 59. In response to a filter selecting signal SG from the control unit 12, the multiplexor 56 selects one of the rectified signals SF1 to SF6 for the six filters 39, reference voltage VR and rectified signal SH given by the output of the element 35. The selected signal is fed to an analog-digital converter 60, which in turn feeds a digital signal to the control unit 12. In response to selecting signals, the control unit 12 derives, as desired, digital signals which represent the intensities of reflected lights for the monochromatic lights passing through the filters 39 and having different wavelengths, brightness of the lamp and reference voltage VR. The unit checks the disks for color reactions in the following manner based on the signals.

As already described, each of the disks is checked for color reaction by detecting which of the two colors specified for the disk 45 is formed on the disk. The color of the disk 45 is determined by measuring the intensities of reflected lights from the disk 45 for monochromatic lights of two different wavelengths, calculating the difference or ratio between the measurements and comparing the result with a reference value. The wavelengths of two kinds of monochromatic lights are predetermined and programmed in accordance with the combination of the two kinds of colors specified for the cell 44 concerned.

The disk is checked based on the difference in the following manner (hereinafter referred to as "difference method"). The output levels of the reflected lights from the disk 45 with cell No. n at wavelengths A and B are assumed to be VAn and VBn, and the difference VDn between VAn and VBn is determined. The difference VDn is then compared with a reference value KDn for cell No. n. If, for example, the difference VDn is greater than the reference value KDn, the disk is evaluated as positive ($+$), and if otherwise as negative ($-$).

Alternatively the disk is checked by the following procedure based on the ratio (hereinafter referred to as "ratio method"). The output levels of the reflected lights from the disk 45 with cell No. n at wavelengths A and B are assumed to be VAn and VBn, and the ratio VPn therebetween is calculated. The ratio VPn is then compared with a reference value KPn for cell No. n. If, for example, the ratio VPn is greater than the reference value KPn, the disk is evaluated as positive ($+$), and if otherwise as negative ($-$).

The difference method and the ratio method are changed for each other in any suitable known manner by means such as a change-over switch on the case 24. The reference values KDn and KPn are entered with the keyboard 17 as will be described later. These values can be stored in the ROM 13 in advance.

Depending on the combination of the two colors specified for the disk 45, difficulty may be encountered in checking only with two kinds of wavelengths, in which case the output levels of the reflected lights are measured at three different wavelengths, and the color is determined based on the resulting differences or ratio.

Some disks may develop a color reaction only for a very short period of time upon application of a color forming reagent. Since it is impossible to check such disks automatically, the color is then identified with the unaided eye, and the result is entered with the keyboard 17 as will be described later.

Further depending on the group of bacteria to tested, bacteria are cultured with use of the same disks 45 for two cells 44, to which different color forming reagents are applied for the determination of color. In this case, the combination of the results achieved with these cells 44 affords one or two items of checking results. (Such a mode of checking will be referred to as "exceptional checking.") With the present test system, two cells 44, No. 2 and No. 3, are adapted to afford one item of checking result for the family Enterobacteriaceae. Accordingly fifteen cells 44 are used for fourteen checking items. No. 1 cell 44 corresponds to item No. 1, No. 2 and No. 3 cells 44 to item No. 2, and Nos. 4 to 15 cells 44 to items Nos. 3 to 14, respectively. In the case of bacteria not utilizing glucose, two cells 44, No. 14 and No. 15, afford two checking results, so that Nos. 1 to 18 cells correspond to items Nos. 1 to 18, respectively.

Figure 7:
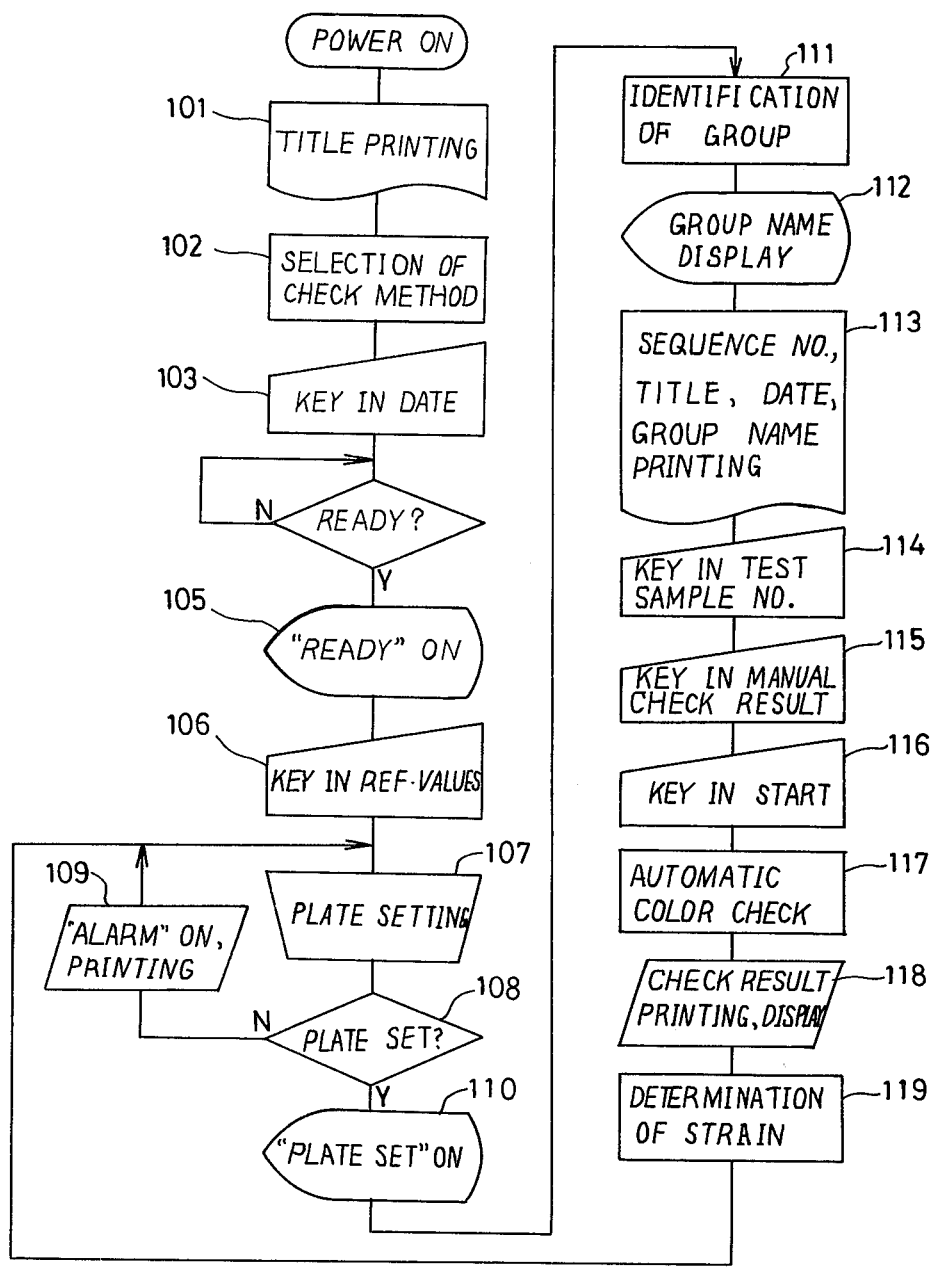
FIG. 7 is a flow chart showing the operation of the preferred embodiment.

The operation of the present test system will be described below with reference to the flow chart of FIG. 7.

Step 101

When the power supply is turned on, a title is automatically printed.

Step 102

The checking method, i.e. the difference method or the ratio method, is selected automatically with reference to the aforementioned change-over switch.

Step 103

The date is keyed in in response to an inquiry from the printer 22. The date data is fed to the number indicator 18 and to the printer 22.

Step 104

The system is checked as to whether it is ready for operation, e.g. whether or not the lamp 36 has been warmed up. If ready, step 105 follows.

Step 105

An indicator lamp 19 goes on, indicating "READY."

Step 106

The reference value KDn or KPn is keyed in in response to an inquiry from the printer 22. The value is entered for each cell (cell number) for either of the two groups of bacteria to be tested. The data is given to the number indicator 18 and to the printer 22.

Step 107

A culture plate 25 containing bacteria incubated for a predetermined period of time is set in the plate accommodating portion of the case 24, and the lid 26 is closed.

Step 108

The culture plate 25 is checked as to whether or not it is set in position. If it is properly set, step 110 follows; otherwise step 107 follows.

Step 109

An indicator lamp 19 goes on, indicating "ALARM." The information that the plate 25 is not properly set is printed. Step 107 is repeated.

Step 110

Another indicator lamp 19 goes on, indicating "PLATE SET."

Step 111

The test group is identified (whether the family Enterobacteriaceae or bacteria not utilizing glucose) automatically based on the number of cells 44 containing disks 45.

Step 112

The group name is displayed with another indicator lamp 19.

Step 113

The sequence number, title, date and group name are printed.

Step 114

The test sample number is keyed in in response to an inquiry from the printer 22. The data is given to the number indicator 18 and to the printer 22.

Step 115

Only the cell 44 which is not automatically checkable is checked manually, that is the color of the disk is determined with the unaided eye as already described. In response to an inquiry from the printer 22, the manual check result is keyed in, in terms of "+" or "−".

Step 116

Instructions to start measurement are given with the keyboard 17.

Step 117

The colors of the disks 45 in the cells 44 are automatically determined in the manner already described, starting with No. 1 cell 44 in succession except for the cell or cells 44 manually checked. The aforementioned exceptional checking is also done automatically at this time.

Step 118

The checking results are printed and displayed. The printer 22 prints the results in the order of checking item numbers in terms of "+" or "−" and also in the form of a code. The code is displayed on the number indicator 18. The results are encoded in the following manner. The check result for each item is expressed by "1" for positive (+) or "0" for negative (−). Such digits representing the results are arranged in the order of the item numbers, the first digit representing the result of item No. 1, the last digit respresenting that of the last item number. The binary string thus obtained is divided into groups of three digits, from the last digit position toward the first, to form an identification code by octal representation. For example, when the results for enterobacteriaceae are positive for item Nos. 1, 2, 5, 8, 9 and 13 and negative for the other items, the results are expressed as "+ + − − + − − + + − − − − + −" and encoded as "31142". Further when the results for a bacterium not utilizing glucose are positive for item Nos. 1, 2, 4, 7, 8, 15 and 18 and negative for the other items, the results are expressed as "+ + − + − − + + − − − − − − + − − +" and "646011".

Step 119

The strain of bacteria tested is determined based on the results thus obtained.

When the test system is connected to neither of the strain determining system 27 and paper tape puncher 28, the strain is determined manually from the identification code with reference to a code table.

When the system is connected to the strain determining system 27, the check results are fed from the control unit 12 to the system 27, by which the strain is automatically determined with reference to a code table stored therein. The result obtained is fed to the printer 22.

When the system is connected to the puncher 28, the check results are fed to a paper tape. The strain can be determined automatically by feeding the information on the tape to a strain determining system which is provided independently of the test system.

The test for one kind of bacteria is thus completed. Step 107 thereafter may follow for another culture plate.

Although the above embodiment has been described for the family Enterobacteriaceae and bacteria which do not utilize glucose, the test system is usable also for identifying groups of other bacteria. The number of cells 44 is variable as desired.

While a relatively small number of filters 39 are used for the foregoing embodiment for checking the disk as to which of the two colors specified therefor is formed on the disk, such colors can be identified with use of a very large number of filters by measuring the intensities of reflected lights for many different wavelengths and suitably processing the measurements.

The arrangement of the light source assembly 31 and the photoelectric elements 34, 35 can be modified suitably. Such photoelectric elements may be adapted to receive transmitted light for use with some types of specimens. The light incident on the specimen, as well as the light reflected from or passing through the specimen, need not always be guided by optical fibers.

What is claimed is:

1. A test system for identifying bacteria comprising a transparent culture plate having a plurality of cells adapted to receive said bacteria, a light source applying light to specimen bacteria in each of the cells of the culture plate, a plurality of photoelectric elements equal to the number of cells for converting into an electric signal the light reflected from each specimen, a rotatable support carrying a plurality of circumferentially spaced filters for producing monochromatic lights of different wavelengths from said light source disposed between said light source and said specimens, said support being continuously rotatable at a predetermined speed in a predetermined direction to permit the filters to be selected one after another, means actuated by said rotatable support for producing synchronizing signals indicative of the operative filter, and control means responsive to said synchronizing signals connected to said photoelectric elements for deriving therefrom electric signals in response to the monochromatic lights passing through a specified number of the filters, which identify said bacteria by the color of the specimen based on the electric signals.

2. A test system according to claim 1 in which the control means derives from the photoelectric element electric signals in response to the monochromatic lights passing through at least two filters to identify said bacteria by the color of the specimen based on the difference between the electric signals.

3. A test system according to claim 1 in which the control means derives from the photoelectric element electric signals in response to the monochromatic lights passing through at least two filters to identify said bacteria by the color of the specimen based on the ratio between the electric signals.

4. A test system according to claim 1 in combination with a bundle of optical fibers positioned at one end adjacent said rotary support and at their other end individually guiding the monochromatic lights passing through the filters to each specimen and optical fibers individually disposed between each specimen and a photoelectric element for guiding to the photoelectric element the light reflected from said specimen.

5. A test system according to claim 1 in which the specimen comprises a paper disk impregnated with a reagent, and the light reflected from the disk is guided to the photoelectric element.

6. A test system according to claim 1 in which said control means comprises a first multiplexor connected to the output of said photoelectric elements for selecting signals therefrom, a second multiplexor, an amplifier interconnecting the output of said first multiplexor with the input of said second multiplexor, a counter actuated by said synchronizing signals sequentially activating the output terminals of said second multiplexor, whereby output terminals provide signals proportional to reflected light derived individually from said filters, a third multiplexor whose input is connected to the output terminals of said second multiplexor, and an analog-digital converter connected to the output of said third multiplexor to produce signals representative of light from the individual specimens.

7. A test system according to claim 2 in combination with a bundle of optical fibers positioned at one end adjacent said rotary support and at their other end individually guiding the monochromatic lights passing through the filters to each specimen and optical fibers individually disposed between each specimen and a photoelectric element for guiding to the photoelectric element the light reflected from said specimen.

8. A test system according to claim 3 in combination with a bundle of optical fibers positioned at one end adjacent said rotary support and at their other end individually guiding the monochromatic lights passing through the filters to each specimen and optical fibers individually disposed between each specimen and a photoelectric element for guiding to the photoelectric element the light reflected from said specimen.

9. A test system according to claim 2 in which the specimen comprises a paper disk impregnated with a reagent, and the light reflected from the disk is guided to the photoelectric element.

10. A test system according to claim 3 in which the specimen comprises a paper disk impregnated with a reagent, and the light reflected from the disk is guided to the photoelectric element.

11. A test system according to claim 4, in which the specimen comprises a paper disk impregnated with a reagent, and the light reflected from the disk is guided to the photoelectric element.